United States Patent

Koizumi et al.

Patent Number: 5,539,127
Date of Patent: Jul. 23, 1996

[54] 7-SUBSTITUTED OXA- OR AZASTEROID COMPOUND

[75] Inventors: Naoyuki Koizumi, Sagamihara; shigehiro Takegawa; Shigeki Iwashita, both of Kawasaki; Tomoko Kawachi, Inagi; Fumiko Inoue, Usa; Seijiro Honma, Yokohama; Hiroo Takahashi, Sagamihara; Mamoru Mieda, Ebina; Kaoru Ueda, Kawasaki; Kenyu Shibata, Tokyo, all of Japan

[73] Assignee: Teikoku Hormone Mfg. Co., Ltd., Tokyo, Japan

[21] Appl. No.: 403,867

[22] PCT Filed: Sep. 29, 1993

[86] PCT No.: PCT/JP93/01390

§ 371 Date: Mar. 24, 1995

§ 102(e) Date: Mar. 24, 1995

[87] PCT Pub. No.: WO94/07908

PCT Pub. Date: Apr. 14, 1994

[30] Foreign Application Priority Data

Sep. 30, 1992 [JP] Japan ..................... 4-283616

[51] Int. Cl.$^6$ ................. A61K 31/565; C07J 31/00
[52] U.S. Cl. ................. 549/384; 546/61
[58] Field of Search ............... 546/61; 549/276, 549/384; 548/426

[56] References Cited

U.S. PATENT DOCUMENTS

| | | | |
|---|---|---|---|
| 4,116,978 | 9/1978 | Cimarusti et al. | 549/384 |
| 4,235,893 | 11/1980 | Brodie et al. | 424/243 |
| 4,591,585 | 5/1986 | Kerb et al. | 514/177 |
| 4,757,061 | 7/1988 | Faustini et al. | 514/177 |
| 4,808,616 | 2/1989 | Buzzetti et al. | 514/177 |
| 5,219,879 | 6/1993 | Ko et al. | 549/384 |
| 5,227,375 | 7/1993 | Labrie et al. | 514/172 |

FOREIGN PATENT DOCUMENTS

| | | |
|---|---|---|
| 3322285 | 12/1984 | Germany . |
| 3622841 | 1/1987 | Germany . |
| 60-13796 | 1/1985 | Japan . |
| 61-189295 | 8/1986 | Japan . |
| 62-12797 | 1/1987 | Japan . |
| 5-148294 | 6/1993 | Japan . |
| 2171100 | 8/1986 | United Kingdom . |
| WO91/12206 | 8/1991 | WIPO . |

OTHER PUBLICATIONS

Sherwin et al., "*Effects of Steroid D-Ring Modification on Suicide Inactivation and Competitive Inhibition of Aromatase by Analogues of Androsta–1,4–diene–3,17–dione*", Journal of Medicinal Chemistry, 1989, 32, pp.651–658.

Brueggemeier et al., "Synthesis and Biochemical Evaluation of Inhibitors of Estrogen Biosynthesis", *Journal of Medicinal Chemistry*, 1978, vol. 21, No. 10, pp. 1007–1011.

Primary Examiner—Nicholas Rizzo
Attorney, Agent, or Firm—Wenderoth, Lind & Ponack

[57] ABSTRACT

A steroid compound represented by the formula

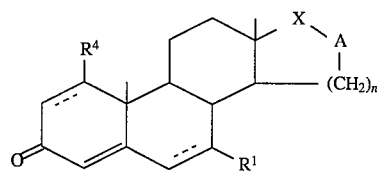

which has an excellent aromatase-inhibiting effect and is useful for preventing or treating diseases caused by estrogens, such as breast cancer, uterine cancer and prostatomegaly. This compound has an oxygen or nitrogen atom as the heteroatom at the position A of the ring D and the 7-position (substituent $R^1$) of the skeleton is substituted by —S—$R^2$ (wherein $R^2$ represents hydrogen, lower alkyl which may be substituted by hydroxy, amino or lower alkoxycarbonyl, lower alkenyl, aralkyl, aryl which may be substituted by halogen, amino, di(lower alkyl)amino, lower alkoxy or lower alkyl, acyl, or lower alkoxycarbonyl), —S(O)m—$R_3$ (wherein $R^3$ represents lower alkyl; and m represents 1 or 2), or aralkyl.

6 Claims, No Drawings

7-SUBSTITUTED OXA- OR AZASTEROID COMPOUND

TECHNICAL FIELD

This invention relates to novel 7-substituted oxa- or azasteroid compounds having an aromatase-inhibiting action, and more detailedly relates to a steroid compound represented by the formula

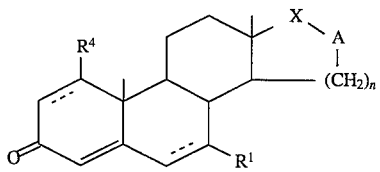

(I)

wherein $R^1$ denotes —S—$R^2$, —S(O)m—$R^3$ or an aralkyl group, wherein $R^2$ denotes a hydrogen atom; a lower alkyl group optionally substituted with a hydroxyl, amino or lower alkoxycarbony group; a lower alkenyl group; an aralkyl group; an aryl group optionally substituted with halogen atom(s), or amino, di-(lower alkyl )amino, lower alkoxy or lower alkyl group(s); an acyl group; or a lower alkoxycarbonyl group, $R^3$ denotes a lower alkyl group, m denotes 1 or 2, $R^4$ denotes a hydrogen atom or —S—$R^5$, wherein $R^5$ denotes a lower alkyl group optionally substituted with a hydroxyl, amino or lower alkoxycarbonyl group; a lower alkenyl group; an aralkyl group; an aryl group optionally substituted with halogen atom(s), or amino, di-(lower alkyl) amino, lower alkoxy or lower alkyl group(s); or an acyl group, X denotes C=O or $CH_2$, A denotes O or NH, n denotes 1 or 2, and the broken lines between the 1- and 2-positions and between the 6- and 7-positions of the steroid skeleton mean that a double bond can exist there, provided that
(a) when A denotes NH, X is assumed to denote C=O,
(b) when $R^1$ denotes —S—$R^2$ or —S(O)m—$R^3$, the bond between the 6- and 7-positions is assumed to denote a single bond, and
(c) when $R^4$ denotes —S—$R^5$, the bond between the 1- and 2-positions is assumed to denote a single bond.

BACKGROUND OF INVENTION

Biosynthesis of estrogens can be carried out by means such that androgens are subjected to oxidation and elimination of formic acid by an enzyme called aromatase, and aromatized. Therefore, if the action of aromatase can effectively be inhibited, it is expected to be useful for treatment of diseases caused by estrogens, and in line with this expectation, several aromatase inhibitors have already been found to be effective for treatment of breast cancer and prostatic hypertrophy.

Aromatase inhibitors are also effective for treatment of other diseases caused by estrogens, for example uterine cancer, ovarian cancer, endometriosis, male gynecomastia, male e infertility related to oligospermia, etc.

As known steroid aromatase inhibitors, there have, for example, been known testolactone (Merck Index, 10th edition, 8999), 4-hydroxy-4-androstene-3,17-dione and its esters (U.S. Pat. No. 4,235,893), 1-alkylandrosta-1,4-diene-3,17-dione derivatives (Japanese Laid-Open Patent Publication No. 13796/1985), 4-substituted androstene-3,17-dione derivatives (Japanese Laid-Open Patent Publication No. 189295/1986), 6-methyleneandrosta-1,4-diene-3,17-dione derivatives (Japanese Laid-Open Patent Publication No. 12797/1987), 16-oxaandrosta-1,4-diene-3,17-dione (Journal of Medicinal Chemistry, 32, 651, (1989)), 7α-substituted thioandrostenedione derivatives (Journal of Medicinal Chemistry, 21, 1007, (1978)), etc.

However, these steroid aromatase inhibitors, when administered into living bodies, are liable to be inactivated through metabolism, and are still not satisfactory for clinical use.

The present inventors found that a series of steroid compounds wherein a hetero atom is introduced into the ring D part and the 7-position of the steroid skeleton is substituted with a specific substituent have a very excellent aromatase-inhibiting activity, and moreover, are slow to undergo inactivation through metabolism.

DISCLOSURE OF INVENTION

In this description, the term "lower" means that the carbon atom number of groups or compounds to which this term is attached is 6 or less, preferably 4 or less.

In the above formula (I), the "lower alkyl group" includes, for example, methyl, ethyl, n-propyl, isopropyl, n-butyl, sec-butyl, tert-butyl, n-pentyl, n-hexyl groups, etc., the "lower alkoxy group" includes, for example, methoxy, ethoxy, n-propoxy, n-butoxy groups, etc., the "lower alkenyl group" includes, for example, vinyl, all yl groups, etc., the "lower alkoxycarbonyl group" includes, for example, methoxycarbonyl, ethoxycarbonyl, isopropoxycarbonyl groups, etc., and the "aralkyl group" includes, for example, benzyl, 4-methoxybenzyl, phenethyl groups, etc.

The "lower alkyl group optionally substituted with a hydroxyl, amino or lower alkoxycarbonyl group" includes, for example, besides the above-mentioned unsubstituted lower alkyl groups, 2-hydroxyethyl, 3-hydroxypropyl, 2-aminoethyl, 3-aminopropyl, methoxycarbonylmethyl, methoxycarbonylethyl, ethoxycarbonylmethyl, ethoxycarbonylethyl, groups, etc., and the "aryl group optionally substituted with halogen atom(s), or amino, di-(lower alkyl)amino, lower alkoxy or lower alkyl group(s) includes, for example, phenyl, 1-naphthyl, 2-naphthyl, 4-chlorophenyl, 2-aminophenyl, 4-aminophenyl, 4-amino-1-naphthyl, 4-dimethylaminophenyl, 4-alkoxyphenyl, 4-alkylphenyl groups, etc.

The "acyl group" is the residue part remaining after at least one OH was removed from an organic acid such as a mono- or polycarboxylic acid, and specifically include groups of the formula —$COR^6$. Herein, $R^6$ means a hydrogen atom; a lower alkyl group optionally substituted with a halogen atom, an amino group, a carboxyl group, a lower alkoxycarbonyl group, a lower alkanoyloxy group, a carbamoyl group or an aryl group; a lower alkenyl group optionally substituted with an aryl group; a lower cycloalkyl group; an aryl group optionally substituted with lower alkyl group(s), lower alkoxy group (S) or halogen atom(s); an amino group optionally substituted with one or two lower alkyl groups; etc.

Specific examples of the "acyl group" includes formyl, acetyl, propionyl, butyryl, trifluoroacetyl glycyl, 3-carboxypropionyl, 3-ethoxycarbonylpropionyl acetoxyacetyl, phenylacetyl, acryloyl, benzoyl, p-methoxybenzoyl, p-methylbenzoyl, p-chlorobenzoyl, carbamoyl, N,N-dimethylcarbamoyl, N,N-diethylcarbamoyl etc.

A preferred group of compounds in the above formula (I) are compounds of the formula (I) wherein $R^1$ denotes —S—$R^2$ or —S(O)m—$R^3$.

Another preferred group of compounds are compounds of the formula (I) wherein A denotes O and n denotes 2.

In the compounds of the above formula (I) of this invention, when the bonds between the 1- and 2-positions and/or between the 6- and 7-positions denote single bonds, the substituents $R^1$ and —S—$R^5$ may bind to any of the α-position and the β-position, but in view of pharmacological activities, compounds wherein the substituents bind to the α-positions are particularly preferable (all the chemical formulae described in this description, regardless of whether the substituents at the 1- and 7-positions bind to the α-position or the β-position, are expressed by solid lines).

As representative examples of the compounds of the above formula (I) provided by this invention, the following ones, besides those described in the later-described examples, can be mentioned.

7α-mercapto-D-homo-17-oxaandrost-4-en-3-one,
7α-(methylthio)-D-homo-17-oxaandrost-4-ene-3,17a-dione,
7α-(butylthio)-D-homo-17-oxaandrosta-1,4-diene-3,17a-dione,
7α-[(2-hydroxyethyl)thio]-D-homo-17-oxaandrosta-1,4-dien-3-one,
7α-(benzylthio)-D-homo-17-oxaandrosta-1,4-diene-3,17a-dione,
7α-[(1-naphthyl)thio]-D-homo-17-oxaandrost-4-ene-3,17a-dione,
7α-[(4-chlorophenyl)thio]-D-homo-17-oxaandrosta-1,4-diene-3,17a-dione,
7α-[(2-aminophenyl)thio]-D-homo-17-oxaandrost-4-ene-3,17a-dione,
7α-[(4-aminophenyl)thio]-D-homo-17-oxaandrosta-1,4-diene-3,17a-dione,
7α-[(4-dimethylaminophenyl)thio]-D-homo-17-oxaandrosta-1,4-dien-3-one,
7α-[(4-methoxyphenyl)thio]-D-homo-17-oxaandrosta-1,4-diene-3,17a-dione,
7α-[(4-methylphenyl)thio]-D-homo-17-oxaandrost-4-ene-3,17a-dione,
7α-(propionylthio)-D-homo-17-oxaandrosta-1,4-dien-3-one,
7α-(ethylsulfinyl)-D-homo-17-oxaandrosta-1,4-diene-3,17a-dione,
7α-mercapto-16-oxaandrosta-1,4-diene-3,17-dione,
7α-mercapto-16-oxaandrosta-1,4-dien-3-one,
7α-(ethylthio)-16-oxaandrosta-1,4-diene-3,17-dione,
7α-[(2-hydroxyethyl)thio]-16-oxaandrost-4-ene-3,17-dione,
7α-[(4-aminophenyl)thio]-16-oxaandrost-4-en-3-one,
7α-[(4-methoxyphenyl)thio)-16-oxaandrosta-1,4-diene-3,17-dione,
7α-(acetylthio)-16-oxaandrost-4-ene-3,17-dione,
7α-(acetylthio)-16-oxaandrosta-1,4-dien-3-one,
7α-(N,N-dimethylcarbamoylthio)-16-oxaandrosta-1,4-diene-3,17-dione,
7α-(methylsulfinyl)-16-oxaandrosta-1,4-diene-3,17-dione,
1α-(acetylthio)-7α-mercapto-D-homo-17-oxaandrost-4-ene-3,17a-dione,
1α-(acetylthio)-7α-[(4-aminophenyl)thio]-D-homo-17-oxaandrost-4-en-3-one,
1α,7α-bis[(2-hydroxyethyl)thio]-D-homo-17-oxaandrost-4-ene-3,17a-dione,
1α,7α-bis[(2-aminoethyl)thio]-D-homo-17-oxaandrost-4-en-3-one,
1α,7α-bis(ethoxycarbonylmethylthio)-D-homo-17-oxaandrost-4-ene-3,17a-dione,
1α,7α-bis[(4-dimethylaminophenyl)thio]-D-homo-17-oxaandrost-4-en-3-one,
1α,7α-bis[(4-methoxyphenyl)thio]-D-homo-17-oxaandrost-4-ene-3,17a-dione,
1α,7α-bis(N,N-dimethylcarbamoylthio)-D-homo-7-oxaandrost-4-en-3-one,
7α-mercapto-16-azaandrosta-1,4-diene-3,17-dione,
7α-(methylthio)-16-oxaandrosta-1,4-diene-3,17-dione,
7α-[(4-aminophenyl)thio]-16-azaandrost-4-ene-3,17-dione,
7α-(acetylthio)-16-oxaandrosta-1,4-diene-3,17-dione,
7α-(benzoylthio)-16-azaandrost-1,4-ene- 3,17-dione,
7α-mercapto-17-aza-D-homoandrosta-1,4-diene-3,17a-dione,
7α-(acetylthio)-17-aza-D-homoandrost-4-ene-3,17a-dione.

According to this invention, a compound of the above formula (I) wherein the symbol $R^1$ denotes —S—$R^2$ (a) can be prepared by reacting a compound of the formula 1a

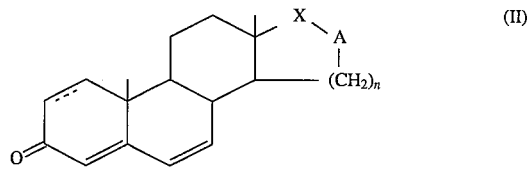

wherein, X, A and n have the same meanings as defined above,
with compound of the formula $$HS—R^{21} \qquad (III)$$

ally substituted with a hydroxy, amino or lower alkoxycarbonyl group; a lower alkenyl group; an aralkyl group; an aryl group optionally substituted with halogen atom(s), or amino, di-(lower alkyl) amino, lower alkoxy or lower alkyl group(s); or an acyl group, and, if desired, subjecting the resultant compound of the formula

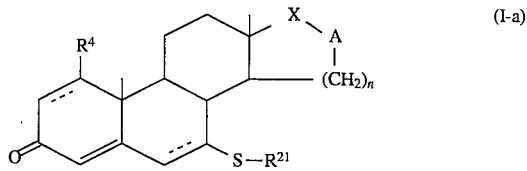

wherein, $R^{21}$, $R^4$, X, A and n have the same meanings as defined above,
to any reaction selected from
(i) a reaction to convert the 7-position to a mercapto group,
(ii) a reaction to convert the 7-position to a mercapto group, and then further convert it to an optionally substituted lower alkylthio group, an acylthio group or a lower alkoxycarbonylthio group, and
(iii) a reaction to eliminate the group $R^4$ at the 1-position to introduce a double bond between the 1- and 2-positions.

Further according to this invention, a compound of the aboveformula (I) wherein the symbol $R^1$ denotes —S(O)m—$R^3$ (b) can be prepared by oxidizing a compound represented by the formula

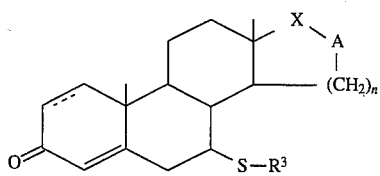

(I-b)

wherein, $R^3$, X, A and n have the same meanings as defined above,
and, if desired, subjecting the resultant compound of the formula

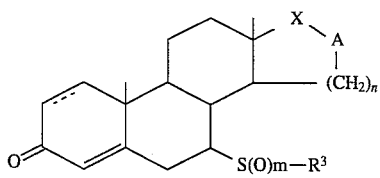

(I-c)

wherein, $R^3$, m, X, A and have the same meanings as defined above, (iv) a reaction to convert the 1-position to —S—$R^5$.

Further according to this invention, a compound above formula (I) wherein the symbol $R^1$ denotes an aralkyl group (c) can be prepared by subjecting a compound of the formula

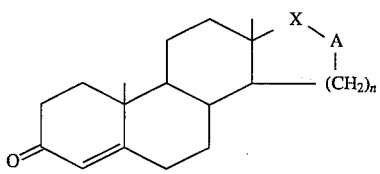

(IV)

wherein, X, A and n have the same meanings as defined above,
to any reaction selected from (v) a reaction to introduce an aralkyl group to the 7-position, and (vi) a reaction to introduce an aralkyl group to the 7-position and introduce a double bond between the 6- and 7-positions, and, if desired, subjecting the resultant compound of the formula

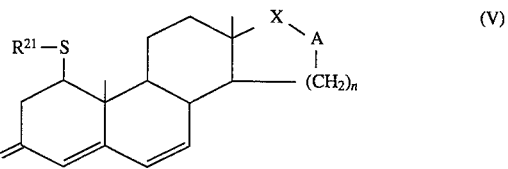

(I-d)

wherein, $R^{11}$ denotes an aralkyl group, and X, A and n have the same meanings as defined above, to any reaction selected from (vii) a reaction to introduce a double bond between the 1- and 2-positions, and (viii) a reaction to introduce a double bond between the 1- and 2-positions, and convert the 1-position to a group —S—$R^5$.

In the above process (a), the reaction of the compound of the formula (II) with the compound of the formula (III), when $R^{21}$ denotes an acyl group, can usually be carried out in the absence of solvents or in a solvent such as acetic acid, at room temperature to the reflux temperature of the reaction mixture, preferably at the reflux temperature of the reaction mixture.

On the other hand, when $R^{21}$ denotes a group other than an acyl group the reaction can usually be carried out in an inert solvent such ass dioxane, tetrahydrofuran, methanol or ethanol, in the presence of an alkali metal alkoxide such as sodium methoxide or sodium ethoxide; an alkali metal such as sodium metal or potassium met al; an alkali metal hydride such as sodium hydride or potassium hydride. Proper reaction temperature in this case is, generally, 0° C. to the reflux temperature of the reaction mixture.

As to the use ratio o f the compound of the formula (III) to the compound of the formula (II), it is generally advantageous to use the formula (III) in an amount of at least one tool, usually of the order of 2 to 20 mols per mol of the compound of the formula (II). It is suitable to use about 1.5 to 15 mols of the alkali metals per mol of the compound of the formula (I-a)

Thus, a compound of the above formula (I-a) of this invention is formed.

When this reaction is performed under a mild condition, for example at a reaction temperature of 0° C. to around room temperature, using as a starting material a compound of the formula (II) wherein a double bond exists between the 1- and 2-positions, a compound of the following formula (V)

wherein, and n have the same meanings as defined above, is also formed, besides the compound of the above formula 1a (I-a).

The obtained compound of the formula (I-a) can, if desired, be converted to another compound aimed at by this invention, by subjecting the former compound to any reaction selected from the above-mentioned reactions of (i), (ii) and (iii).

The conversion of the 7-position to a mercapto group in the reaction of the above (i) can readily be performed by subjecting a compound whose 7-position is an acylthio group to hydrolysis. The hydrolysis can be performed by a process known per se, for example by treating the compound with an alkali such as sodium hydroxide or potassium hydroxide in a solvent such as tetrahydrofuran, methanol or ethanol.

The conversion of the 7-position from a mercapto group to an optionally substituted lower alkylthio group in the reaction of the above (ii) can readily be performed, for example by treating the raw material compound with a lower alkylating reagent such as an optionally substituted lower alkyl halide, in an inert solvent such as dimethylformamide, dimethyl sulfoxide or tetrahydrofuran, in the presence of an alkali such as sodium hydride or sodium methoxide. The conversion of the 7-position from a mercapto group to an acylthio group or a lower alkoxycarbonylthio group can readily be performed, for example by treating the raw material compound with an acid halide, a lower alkyl halogenocarbonate, an acid anhydride or the like, in an inert solvent such as chloroform, dichloromethane or dioxane, in the presence of an alkali such as pyridine, sodium hydride or sodium methoxide.

In the reaction of introduction of a double bond between the 1- and 2-positions in the (iii), different reaction conditions are used between the case where the substituent $R^4$ at the 1-position denotes a hydrogen atom and the case where $R^4$ denotes —S—$R^5$.

Namely, when the substituent R at the 1-position denotes a hydrogen atom, the reaction can, usually be performed by dehydrogenating a compound of the formula (I-a) in an inert solvent such as dioxane or benzene under reflux, using 2,3-dichloro-5,6-dicyano-1,4-benzoquinone (DDQ).

On the other hand, when the substituent $R^4$ at the 1-position denotes —S—$R^5$ the group —S—$R^5$ at the 1-position can be eliminated by heating a compound of the formula (I-a) or treating it with an alkali.

The treatment with heating can, for example, be performed in an inert solvent such as dimethyl formamide, dimethyl sulfoxide or toluene under reflux, if desired in the presence of an acid such as acetic acid or p-toluenesulfonic acid.

The treatment with an alkali can, for example, be performed in an inert solvent such as tetrahydrofuran, dioxane or methanol, in the presence of an alkali such as sodium methoxide or sodium hydroxide. In this reaction, when a compound of the formula (I-a) wherein $R^{21}$ denotes an acyl group is used, not only the group —S—$R^5$ at the 1-position is eliminated, but also the acylthio group at the 7-position is converted to a mercapto group through hydrolysis with the alkali.

According to the above mentioned process (b), the oxidation of the compound of the formula (I-b) can usually be performed by treating it with an oxidizing agent such as m-chloroperbenzoic acid or peracetic acid, in an inert solvent such as benzene, toluene or chloroform.

Proper reaction temperature is generally on the order of 0° to 50° C., preferably from under ice cooling to around room temperature, and it is usually suitable to make the ratio of the oxidizing agent on the order of 0.5 to 3 mols per mole of the compound of the above formula (I-b).

Thus, a compound of the above formula (I-c) of this invention is formed.

It is possible in this invention to prepare a desired compound of the formula (I-c) wherein m is 1 and/or 2, by appropriately selecting the amount of the oxidizing agent to be used and reaction conditions.

The resultant compound of the formula (I-c) can, if desired, be converted to another compound of this invention by subjecting it to the reaction of the above (iv).

The conversion of the hydrogen atom at the 1-position to the group —S—$R^5$ in the above reaction of (iv) can be performed in the same manner as in the reaction of the compound of the formula (II) with the compound of the formula (III) in the above process (a).

According to the above-mentioned process (c), a compound of the above formula (I-d) of this invention wherein the 7-position is substituted with an aralkyl group can be prepared by subjecting a compound of the above formula (IV) to either the reaction of (v) or the reaction of (vi).

The introduction of an aralkyl group into the 7-position in the abovereaction of (v) can be performed by first introducing a double bond between the 6- and 7-positions of the compound of the above formula (IV), and then aralkylating the resultant compound.

The introduction of a double bond between the 6- and 7-positions can, usually, be performed by dehydrogenating the compound of the above formula (IV) in t-butanol or xylene under reflux, using 2,3,5,6-tetrachloro-1,4-benzoquinone (chloranil). The succeeding aralkylation can readily be performed, for example by treating the resultant compound with an aralkylmagnesium halide, e.g., benzylmagnesium chloride, in an inert solvent such as tetrahydrofuran, dioxane or diethyl ether, in the presence of cuprous chloride.

When a compound of the formula (IV) wherein X denotes C=O is used as a starting material in this reaction, it is preferable either to previously protect the oxo group at the 17- or 17a-position with an ethylenedioxy group, etc. in the aralkylation, or to first convert the oxo group to a hydroxyl group by reduction with lithium tri-tert-butoxyaluminohydride, etc. in an inert solvent such as tetrahydrofuran, protect the resultant hydroxy compound with an acetyl group, a methoxymethyl group, a tetrahydropyranyl group, t-butyldimethylsilyl group, etc., and then perform the aralkylation. In the above case, after the introduction of the aralkyl group, the 17- or 17a-position is restored to an oxo group by removing the protective group or by removing the protective group and then performing oxidation with Jones reagent.

In the above reaction of (vi), the reaction to introduce an aralkyl group at the 7-position and introduce a double bond between the 6- and 7-positions can be performed by first subjecting a compound of the above formula (IV) to a reaction to protect the oxo group and an isomerization reaction, subjecting the resultant compound to oxidation reaction to introduce an oxo group at the 7-position and then subjecting the resultant compound to aralkylation reaction. In this occasion, after introduction of the aralkyl group, the protective group of the oxo group is eliminated, for example by treating the aralkylated compound with sulfuric acid in dioxane.

Thereby, a compound of the above formula (I-d) of this invention is formed.

The resultant compound of the above formula (I-d) can, if desired, be converted to another compound of this invention by subjecting it to the reaction of (vii) or (viii).

The introduction of a double bond between the 1- and 2-positions in the reaction of the above (vii) can, usually, be performed by dehydrogenating the compound of the formula (I-d) in dioxane or benzene under reflux, using 2,3-dichloro-5,6-dicyano-1,4-benzoquinone (DDQ).

The conversion of the hydrogen atom at the 1-position to the group —S—$R^5$ in the reaction of the above (viii) can be performed in the same manner as in the reaction of the compound of the formula (II) with the compound of the formula (III) in the above method (a).

A compound of the formula (I) of this invention wherein X denotes $CH_2$ can also be prepared by reducing a compound of the formula (I) wherein X denotes C=O with lithium tri-tert-butoxyaluminohydride, diisobutylaluminum hydride, etc. in an inert solvent such as tetrahydrofuran, dioxane or toluene to convert the group X to a hydroxyl group, and further reducing the resultant hydroxy compound with triethylsilane and boron trifluoride-diethyl ether complex in methylene chloride.

Compounds of the above formula (I) prepared according to the processes of this invention can be isolated and purified from the reaction mixtures according to methods known per se, for example by methods such as recrystallization, distillation, column chromatography and/or thin layer chromatography.

EFFECT OF INVENTION

The above-described 7-substituted oxa- or azasteroid compounds of this invention represented by the formula (I) have an excellent aromatase-inhibiting action, and are effective for treatment of diseases caused by estrogens, for example, breast cancer, uterine cancer, ovarian cancer, endometriosis, male gynecomastia, prostatic hypertrophy, male infertility related to oligospermia, etc.

The results of in vitro and in vivo tests on an aromatase-inhibiting action of compounds of the formula (I) of this invention are set forth below.

(1) Assay of aromatase-inhibiting action (in vitro)

Human placental microsome (centrifuged at 105,000×g for 60 minutes) was prepared, according to the method of Ryan (The Journal of Biological Chemistry, 234, 268–272, (1959)). The microsome was used after it was washed twice with 0.5 mM dithiothreitol solution, freeze dried, and stored at −20° C.

The aromatase-inhibiting action was assayed according to the method developed by Tompson and Siiteri (Journal of Biological Chemistry, 249, 5373–5378, (1974)). Namely, the method comprises quantitatively determining $^3H_2O$ released through aromatization of [1,2-$^3$H]androstenedione. The experiment using the enzyme was performed in 67 mM phosphate buffer (pH 7.5) so that the final amount of the incubation solution could be 0.5 ml. The incubation solution contained 180 μM of NADPH, 2μM of [1,2-$^3$H]androstenedione, 150 μg of freeze dried human placental microsome, 25 μl of methanol and a test compound in various concentrations. Incubation was performed in the air at 37° C. for 20 minutes, the reaction was terminated with addition of 3 ml of chloroform, and the mixture was stirred for 40 seconds. The mixture was centrifuged at 700×g for 10 minutes, 0.3 ml of the aqueous solution was taken from the supernatant, the scintillation mixture was added, and the amount of $^3H_2O$ formed was measured.

The results are shown in the following Table 1.

TABLE 1

| Compound | $IC_{50}$ (μM) |
| --- | --- |
| Example 1 | 2.3 |
| Example 8 | 0.4 |
| Example 16 | 0.5 |

(2) Assay of aromatase-inhibiting action (in vivo)

Aromatase-inhibiting action was assayed according to the method developed by G. H. Deckers and A. H. W. M. Schuurs (Journal of Steroid Biochemistry, 32, 625–631, (1989)).

Namely, groups of mature female rats at one week after enucleation of the pituitary gland were used, each group consisting of 8 to 10 animals. 16 mg/kg of dehydroepiandrosterone sulfate (DHEAS) and 5 ml/kg of a solvent (physiological saline containing 2% polysorbate 80), or DHEAS and 2 mg/kg of a test compound suspended in the solvent were orally administered to each rat once a day for the succeeding 4 days. For 6 days starting from the next day of the first administration, vaginal smear was sampled and observed by a microscope after being stained with Giemsa staining solution. Cornification of the vaginal smear with DHEAS was observed from 3 days after the first administration, and its action disappeared 6 days thereafter. Therefore, the cornification smear number was assumed to be the total of 3 days from the third day to fifth day after the initiation of administration. A cornification-inhibiting action with a test compound was expressed as the rate against cornification in the solvent administration group.

In this connection, the cornification of vaginal smear is caused by estrogens biosynthesized from DHEAS by aromatase, and therefore, when aromatase is inhibited, inhibition of cornification is observed.

The results are shown in the following Table 2.

TABLE 2

| Compound | Inhibition rate (%) |
| --- | --- |
| Example 8 | 68.2 ± 13.6 |
| Example 16 | 70.6 ± 15.6 |
| Example 43 | 70.6 ± 15.6 |

Thus, the compounds of this invention represented by the formula (I) can be orally administered or parenterally administered (e.g., intramuscularly injected, intravenouly injected, rectally administered, percutaneously administered, etc.) as an agent for inhibiting biosynthesis of estrogens, for treatment of human beings or other mammals.

The compounds of this invention, when used as pharmaceuticals, can be formulated, together with pharmaceutically acceptable nontoxic additives, into any of dosage forms of solid forms (e.g., tablets, hard gelatin capsules, soft capsules, granules, powders, fine granules, pills, troches, etc.), semisolid forms (e.g., suppositories, ointments, etc.) and liquid forms (e.g., injections, emulsions, suspensions, lotions, sprays, etc.), in accordance with their uses.

Nontoxic additives usable for the above preparations include, for example, starches, gelatin, glucose, lactose, fructose, real rose, magnesium carbonate, talc, magnesium stearate, methylcellulose, carboxymethylcellulose or its salts, gum arabic, polyethylene glycol, p-hydroxybenzoic acid alkyl esters, syrups, ethanol, propylene glycol, Vaselines, Carbowaxes, glycerol, sodium chloride, sodium sulfite, sodium phosphate, citric acid, etc. The pharmaceuticals can also contain another therapeutically useful pharmaceutical. The contents of the compounds of this invention in the pharmaceuticals vary depending on their dosage forms, etc., but, generally, it is desirable to contain the compounds of this invention at concentrations of 0.1 to 50 weight % in the case of solid and semisolid forms, and at concentrations of 0.05 to 10 weight % in the case of liquid forms.

The doses of the compounds of this invention can be widely varied in accordance with the kind of mammals including human beings as subjects, administration routes, the seriousness of symptoms, diagnoses of doctors, etc., but, generally, the doses can be within the range of 0.1 to 100 mg/kg, preferably 1 to 50 mg/kg. However, it is of course possible to administer an amount smaller than the lower limit of the above range or an amount larger than the upper limit in accordance with the seriousness of the symptoms of patients, diagnoses of doctors, etc. The above doses can be administered once a day or several times in divisions per day.

EXAMPLE

This invention is further specifically described below by examples and preparation examples.

Example 1

To a mixture of 100 mg of D-homo-17-oxaandrosta-4,6-diene-3,17a-dione, 0.15 ml of 4-aminothiophenol and 1.5 ml of dioxane was added 5 mg of sodium metal, and the mixture was stirred in an atmosphere of nitrogen at room temperature for 5 days. Water was added to the reaction mixture, and the product was extracted with ethyl acetate. The extract was washed with saturated saline, and dried over anhydrous magnesium sulfate. The sol vent was distilled off, and the resultant crude product was purified by TLC [developing solvent, chloroform:acetone (19:1)] to give 42 mg of 7α-[(4-aminophenyl)thio]-D-homo-17-oxaandrost-4-ene-3,17a-dione.

$^1$H-NMR (CDCl$_3$, δ): 1.20 (3H, s), 1.26 (3H, s), 3.43 (1H, m), 4.0~4.7 (2H, m), 5.67 (1H, s), 6.8~7.5 (4H, m) MS (m/z): 425 (M$^+$), 409

Example 2

0. 13 ml of Jones reagent was added dropwise at 0° C. to a mixture of 100 mg of 7α-benzyl-17aξ-hydroxy-D-homo-17-oxaandrost-4-en-3-one and 8.5 ml of acetone, and the mixture was stirred for 10 minutes. Water was added to the reaction mixture, and the product was extracted with ethyl acetate. The extract was washed with aqueous 5% sodium bicarbonate solution and saturated saline, and dried over anhydrous magnesium sulfate. The solvent was distilled off, and the resultant crude product was purified by TLC [developing solvent, chloroform:acetone (19:1)] to give 48 mg of a-benzyl-D-homo-17-oxaandrost-4-ene-3,17a-dione.

$^1$H-NMR (CDCl$_3$, δ): 1.22 (3H, s), 1.30 (3H, s), 4.0~4.7 (2H, m), 5.72 (1H, s), 6.9~7.5 (5H, m) MS (m/z): 392 (M$^+$), 377, 301

Example 3

A mixture of 50 mg of D-homo-17-oxaandrost-4,6-dien-3-one and 0.2 ml of thioacetic acid was refluxed for 3 hours. The solvent was distilled off, and the resultant crude product was purified by TLC [developing solvent, hexane:ethyl acetate (2:1)] to give 62 mg of 7α-(acetylthio)-D-homo-17-oxaandrost-4-en-3-one.

$^1$H-NMR (CDCl$_3$, δ): 1.03 (3H, s), 1.21 (3H, s), 2.33 (3H, s), 3.00, 3.39 (2H, ABq, J=1 1 Hz), 3.33 (1H, m), 4.00 (2H, m), 5.7 1 (1H, d, J=2 Hz) MS (m/z): 362 (M$^+$), 320, 305, 287

Example 4

The same operation as in Example 1 was made using benzylmercaptan in place of 4-aminothiophenol, 1N sulfuric acid was added to the resultant reaction mixture, and the mixture was stirred overnight at room temperature. The product was extracted with ethyl acetate, and the extract was washed with saturated saline and dried over anhydrous sodium sulfate. The solvent was distilled off, and the resultant crude product was purified by TLC [developing solvent, chloroform:acetone (39:1)] to give 7α-(benzylthio)-D-homo-17-oxaandrost-4-ene-3,17a-dione.

$^1$H-NMR (CDCl$_3$, δ): 1.16 (3H, s), 1.17 (3H, s), 2.83 (1H, m), 3.55, 3.70 (2H, ABq, J=14 Hz), 3.8~4.5 (2H, m), 5.78 (1H, br s), 7.1~7.4 (5H, m) MS (m/z): 424 (M$^+$), 409, 333, 302, 287

Example 5

To a mixture of 68 mg of D-homo-17-oxaandrosta-4,6-dien-3-one, 150 mg of 4-aminothiophenol and 2.5 ml of dioxane was added 15 mg of potassium metal, and the mixture was subjected to supersonic wave at room temperature for one hour in an atmosphere of nitrogen. Potassium metal was removed, water was added to the reaction mixture, and the product was extracted with ethyl acetate. The extract was washed with saturated saline, and dried over anhydrous magnesium sulfate. The solvent was distilled off, and the resultant crude product was purified by TLC [developing solvent, benzene:ethyl acetate (4:1)] to give 32 mg of 7α-[(4-aminophenyl)thio]-D-homo-17-oxaandrost-4-en-3-one.

$^1$H-NMR (CDCl$_3$, δ): 1.04 (3H, s), 1.20 (3H, s), 3.05 (1H, d, J=11 Hz), 3.2~3.6 (3H, m), 4.05 (1H, m), 5.62 (1H, s), 7.0~7.4 (4H, m) MS (m/z): 411 (M$^+$), 395, 393

Example 6

A mixture of 6 ml of 2.0M benzylmagnesium chloride tetrahydrofuran solution, 400 mg of cuprous chloride and 15 ml of tetrahydrofuran was stirred at 0° C. for 10 minutes in an atmosphere of nitrogen. To this mixture was added a mixture of 38 mg of D-homo-17-oxaandrosta-4,6-dien-3-one, 5 mg of cuprous chloride and 2.5 ml of tetrahydrofuran, and the mixture was stirred at room temperature for one hour. Diethyl ether, water and 5% hydrochloric acid were added to the reaction mixture, and the organic layer was washed with aqueous 5% sodium bicarbonate solution and saturated saline and dried over anhydrous sodium sulfate. The solvent was distilled off, and the resultant crude product was purified by TLC [developing solvent, chloroform:acetone (19:1)] to give 28 mg of 7α-benzyl-D-homo-17-oxaandrost-4-en-3-one.

$^1$H-NMR (CDCl$_3$, δ): 1.07 (3H, s), 1.22 (3H, s), 3.05, 3.44 (2H, ABq, J=11 Hz), 3.4 2 (1H, m), 4.11 (1H, m), 5.72 (1H, s), 6.9~7.5 (5H, m)

Example 7

The same operations as in Example 3 were made using 50 mg of D-homo-17-oxaandrosta-1,4,6-trien-3-one in place of D-homo-17-oxaandrosta-4,6-dien-3-one, and the resultant crude product was purified by TLC [developing solvent, hexane:ethyl acetate (1:1)] to give 38 mg of 7α-(acetylthio)-D-homo-17-oxaandrosta-1,4-dien-3-one as the more polar product.

$^1$H-NMR (CDCl$_3$, δ): 1.06 (3H, s), 1.26 (3H, s), 2.32 (3H, s), 2.92 (1H, m), 2.99, 3.39 (2H, ABq, J=11 Hz), 3.30 (1H, m), 4.05 (2H, m), 6.03 (1H, br t, J=2 Hz), 6.27 (1H, dd, J=2, 10 Hz), 7.00 (1H, d, J=10 Hz) MS (m/z): 361 (MH$^+$), 318, 284

Further, 12 mg of 1α,7α-bis(acetylthio)-D-homo-17-oxaandrost-4-en-3-one was obtained as the less polar product.

$^1$H-NMR (CDCl$_3$, δ): 1.02 (3H, s), 1.41 (3H, s), 2.3~3.6 (7H, m), 2.36 (3H, s), 2.37 (3H, s), 3.9~4.2 (3H, m), 5.72 (1H, br s) MS (m/z): 393 (M$^+$-COCH$_3$), 361, 360, 318

Further, 15 mg of 1α-(acetylthio)-D-homo-17-oxaandrosta-4,6-dien-3-one was obtained as the further less polar product.

$^1$H-NMR (CDCl$_3$, δ): 1.06 (3H, s), 1.30 (3H, s), 2.32 (3H, s), 2.3~3.6 (5H, m), 3.9~4.3 (2H, m), 5.72 (1H, br s), 6.20 (2H, b r s)

Example 8

A mixture of 42 mg of 1α,7α-bis(acetylthio)-D-homo-17-oxaandrost-4-en-3-one, 0.5 ml of 28% sodium methylate methanol solution and 3 ml of methanol was stirred at room temperature for 40 minutes in an atmosphere of nitrogen. Acetic acid was added to the reaction mixture, the solvent was distilled off, chloroform was added to the residue, and the insoluble matter was filtered off under a stream of nitrogen. The filtrate was concentrated, and the resultant crude product was purified by TLC [developing solvent, hexane:ethyl acetate (1:1)] to give 24 mg of 7α-mercapto-D-homo-17-oxaandrosta-1,4-dien-3-one.

Melting point: 225°–229° C. (dichloromethanethyl acetate)

$^1$H-NMR (CDCl$_3$, δ): 1.07 (3H, s), 1.24 (3H, s), 2.50 (1H dd, J=2, 13 Hz), 3.02, 3.40 (2H, ABq, J=11 Hz), 3.03 (1H, m), 3.40 (2H, m), 4.05 (1H, m), 6.13 (1H, br t, J=2 Hz), 6.29 (1H, dd, J=2, 10 Hz), 7.03 (1H, d, J=10 Hz) MS (m/z): 318 (M$^+$), 284

Elementary analysis: Calculated for C$_{19}$H$_{26}$O$_2$S: C,71.66; H,8.23 Found :C, 71.87; H, 8.39

Example 9

The same operations as in Example 5 were made using 136 mg of D-homo-17-oxaandrosta-1,4,6-trien-3-one in place of D-homo-17-oxaandrosta-4,6-dien-3-one, and the resultant crude product was purified by TLC [developing solvent, benzene:ethyl acetate (1:1)] to give 68 mg of 1α,7α-bis[(4-aminophenyl)thio]-D-homo-17-oxaandrost-4-en-3-one as the more polar product.

$^1$-NMR (CDCl$_3$, δ): 1.05 (3H, s), 1.32 (3H, s), 3.10 (1H, d, J=11 Hz), 3.2~4.3 (7H, m), 5.74 (1H, s), 6.5~7.4 (8H, m)

Further, a mixture of 7α-[(4-aminophenyl)-thio]-D-homo-17-oxaandrosta-1,4-diene-3-one and 1α-[(4-aminophenyl)thio]-D-homo-17-oxaandrosta-4,6-dien-3-one was obtained from the less polar part. This mixture was purified by TLC [developing solvent, chloroform:acetone (9:1)] to give 5 mg of 7α-[(4-aminophenyl)thio]-D-homo-17-oxaandrosta-1,4-dien-3-one as the more polar product.

$^1$H-NMR (CDCl$_3$, δ): 1.06 (3H, s), 1.23 (3H, s), 3.04, 3.40 (2H, ABq, J=11 Hz), 3.2~4.2 (3H, m), 6.05 (1H, br s), 6.29 (1H, dd, J=2, 10 Hz), 7.03 (1H, d, J=10 Hz), 6.4~7.3 (4H, m) MS (m/z): 409 (M$^+$), 285

Further, 9 mg of 1α-[(4-aminophenyl)thio]-D-homo-17-oxaandrosta-4,6-dien-3-one was obtained as the less polar product.

$^1$H-NMR (CDCl$_3$, δ): 1.10 (3H, s), 1.25 (3H, s), 3.08, 3.44 (2H, ABq, J=11 Hz), 3.2~4.3 (3H, m), 5.76 (1H, s), 6.20 (2H, s), 6.4~7.4 (4H, m) MS (m/z): 409 (M$^+$), 285, 284, 248

Example 10

A mixture of 715 mg of 7ξ-benzyl-3,3:17a,17a-bis(ethylenedioxy)-D-homo-17-oxaandrost-5-en-7ξ-ol, 1.8 ml of 5% sulfuric acid and 11 ml of dioxane was stirred at room temperature for 3 hours. Water and aqueous 5% sodium bicarbonate solution were added to the reaction mixture, and the product was extracted with ethyl acetate. The extract was washed with saturated saline, and dried over anhydrous magnesium sulfate. The solvent was distilled off, and the resultant crude product was purified by TLC [developing solvent, chloroform:acetone (9:1)] to give 140 mg of 7-benzyl-D-homo-17-oxaandrosta-4,6-diene-3,17a-dione.

$^1$H-NMR (CDCl$_3$, δ): 1.03 (3H, s), 1.28 (3H, s), 3.66 (2H, s), 3.8~4.6 (2H, m), 5.63 (1H, s), 6.06 (1H, br s), 7.0~7.5 (5H, m) MS (m/z): 390 (M$^+$), 299

Example 11

A mixture of 30 mg of 7-benzyl-17aξ-hydroxy-D-homo-17-oxaandrosta-4,6-dien-3-one, 0.03 ml of triethylsilane, 0.02 ml of boron trifluoridediethyl ether complex and 0.8 ml of methylene chloride was stirred at 0° C. for 2 minutes under a stream of nitrogen. Aqueous 5% sodium bicarbonate solution was added to the reaction mixture, and the mixture was stirred at room temperature for 10 minutes. The product was extracted with ethyl acetate, and the extract was washed with saturated saline and dried over anhydrous magnesium sulfate. The solvent was distilled off, and the resultant crude product was purified by TLC [developing solvent, chloroform:acetone (19:1)] to give 10 mg of 7-benzyl-D-homo-17-oxaandrosta-4,6-dien-3-one.

$^1$H-NMR (CDCl$_3$, δ): 0.95 (3H, s), 1.07 (3H, s), 3.02, 3.41 (2H, ABq, J=11 Hz), 3.3 0 (1H, m), 3.59 (2H, s), 4.02 (1H, m), 5.5 9 (1H, s), 5.99 (1H, br s), 7.0~7.5 (5H, m) MS (m/z): 376 (M$^+$), 285

Example 12

To a mixture of 6 mg of 7α-mercapto-D-homo-17-oxaandrosta-1,4-dien-3-one, 4μ of 28% sodium methylate methanol solution and 0.3 ml of dimethylformamide was added 4μ of methyl iodide, and the mixture was stirred at room temperature for 5 minutes in an atmosphere of nitrogen. Water was added to the reaction mixture, and the product was extracted with ethyl acetate. The extract was washed with saturated saline, and dried over anhydrous magnesium sulfate. The solvent was distilled off, and the resultant crude product was purified by TLC [developing solvent, chloroform:acetone (100:1)] to give 5 mg of 7α-(methylthio)-D-homo17-oxaandrosta-1,4-dien-3-one.

$^1$H-NMR (CDCl$_3$, δ): 1.05 (3H, s), 1.25 (3H, s), 2.01 (3H, s), 2.4~2.9 (2H, m), 3.00, 3.39 (2H, ABq, J=11 Hz), 3.06 (1H, m), 3.40 (1H, m), 4.05 (1H, m, ), 6.11 (1H, br s), 6.27 (1H, dd, J=2, 10 Hz), 7.01 (1H, d, J=10 Hz) MS(m/z) :332 (M$^+$), 284

Example 13

The same operations as in Example 3 were made using 100 mg of D-homo-17-oxaandrosta-4,6-diene-3,17a-dione in place of D-homo-17-oxaandrosta-4,6-dien-3-one, and the resultant crude product was purified by TLC [developing solvent, chloroform:acetone (39:1)] to give 71 mg of 7α-(acetylthio)-D-homo-17-oxaandrost-4-ene3,17a-dione.

$^1$H-NMR (CDCl$_3$, δ): 1.22 (3H, s), 1.26 (3H, s), 2.35 (3H, s), 2.83 (1H, m), 4.0~4.6 (3H, m), 5.73 (1H, d, J=2 Hz) MS (m/z ): 376 (M$^+$), 334, 319, 301, 285

Example 14

A mixture of 33 mg of 7α-(acetylthio)-D-homo-17-oxaandrost-4-ene-3,17a-dione, 1 ml of 1.4N aqueous sodium hydroxide solution and 1 ml of tetrahydrofuran was stirred at 0° C. for 25 minutes. 10% hydrochloric acid was added to the reaction mixture, and the mixture was stirred for one hour. The product was extracted with ethyl acetate, and the extract was washed with saturated saline and dried over anhydrous sodium sulfate. The solvent was distilled off, and the resultant crude crystals were recrystallized from acetone to give 27 mg of 7α-mercapto-D-homo-17-oxaandrost-4-ene-3,17a-dione.

$^1$H-NMR (CDCl$_3$, δ): 1.20 (3H, s), 1.27 (3H, s), 2.93 (1H, m), 3.40 (1H, m), 4.1~4.7 (2H, m), 5.81 (1H, d, J=2 Hz) MS (m/z): 334 (M$^+$), 319, 301, 285

Example 15

The same operations as in Example 3 were made using 20 mg of D-homo-17-oxaandrosta-1,4,6-triene-3,17a-dione in place of D-homo-17-oxaandrosta-4,6-dien-3-one, and the resultant crude product was purified by TLC [developing solvent, chloroform:acetone (50:1)] and then by TLC [developing solvent, benzene:ethylacetate (3:1)] to give 7 mg of 7α-(acetylthio)-D-homo-17-oxaandrosta-1,4-diene-3,17a-dione.

¹H-NMR (CDCl₃, δ)): 1.26 (3H, s), 1.29 (3H, s), 2.35 (3H, s), 2.93 (1H, m), 4.0~4.6 (3H, m), 6.05 (1H, br t, J=2 Hz), 6.29(1H, dd, J=2, 10 Hz), 7.01 (1H, d, J=10 Hz) MS (m/z): 374 (M⁺), 359, 332, 298, 283,

Example 16

The same operations as in Example 14 were made using 5 mg of 7α-(acetylthio)-D-homo-17-oxaandrosta-1,4-diene-3,17a-dione in place of 7α-(acetylthio)-D-homo-17-oxaandrost-4-ene-3,17a-dione, and the resultant crude product was purified by TLC [developing solvent, benzene:ethyl acetate (3:1)] to give 1 mg of 7α-mercapto-D-homo-17-oxaandrosta-1,4-diene-3,17a-dione.

¹H-NMR (CDCl₃, δ): 1.24 (3H, s), 1.30 (3H, s), 2.54 (1H, dd, J=2, 14 Hz), 3.04 (1H, m), 3.43 (1H, m), 4.0~4.6 (2H, m), 6.15 (1H, br t, J=2 Hz), 6.30 (1H, dd, J=2, 10H z), 7.03 (1H, d, J=10 Hz) MS (m/z): 332 (M⁺), 317, 298, 283

Example 17

A mixture of 8 mg of 7α-mercapto-D-homo-17-oxaandrost-4-ene-3,17a-dione, 0.04 ml of pyridine, 0.02 ml of benzoyl chloride and 0.2 ml of methylene chloride was stirred under ice cooling for 60 minutes. Water and aqueous 5% hydrochloric acid solution were added to the reaction mixture, and the product was extracted with ethyl acetate. The extract was washed with water and dried over anhydrous magnesium sulfate. The solvent was distilled off, and the resultant crude product was purified by TLC [developing solvent, benzene:ethyl acetate (3:1)] to give 8 mg of 7α-(benzoylthio)-D-homo-17-oxaandrost-4-ene-3,17a-dione.

¹H-NMR (CDCl₃, δ): 1.26 (3H, s), 1.28 (3H, s), 2.9 (1H, m), 3.9~4.6 (3H, m), 5.73 (1H, d, J=2 Hz), 7.3~8.2 (5H, m)

Example 18

To a mixture of 50 mg of D-homo-17-oxaandrosta-1,4,6-trien-3-one, 0.05 ml of 28% sodium methylate methanol solution and 2 ml of dioxane was added 0.1 ml of thiophenol, and the mixture was stirred at room temperature for 5 minutes in an atmosphere of nitrogen. Water was added to the reaction mixture, and the product was extracted with ethyl acetate. The extract was washed with saturated saline and dried over anhydrous magnesium sulfate. The solvent was distilled off, and the resultant crude product was purified by TLC [developing solvent, benzene:ethyl acetate (4:1)] to give 8 mg of 7α-(phenylthio)-D-homo-17-oxaandrosta-1,4-dien-3-one as the more polar product.

¹H-NMR (CDCl₃, δ): 1.07 (3H, s), 1.24 (3H, s), 2.2~2.9 (2H, m), 3.03 (1H, d, J=11 Hz), 3.2~3.7 (3H, m), 4.00 (1H, m), 6.00 (1H, br s), 6.29 (1H, dd, J=2, 10 Hz), 7.04 (1H, d, J=10 Hz), 7.2~7.5 (5H, m) MS (m/z): 394 (M⁺), 284

Further, 80 mg of 1α,7α-bis(phenylthio)-D-homo-17-oxaandrost-4-en-3-one was obtained as the less polar product.

¹H-NMR (CDCl₃, δ): 1.06 (3H, s), 1.37 (3H, s), 2.4~2.8 (4H, m), 3.07 (1H, d, J=11 Hz), 3.2~3.7 (4H, m), 4.01 (1H, m), 5.71 (1H, br s), 7.1~7.6 (10H, m) MS (m/z): 504 (M⁺), 394, 284

Example 19

The same operations as in Example 18 were made using ethanethiol in place of thiophenol and a dioxane-dimethylformamide mixed solvent in place of dioxane, and the resultant crude product was purified by TLC [developing solvent, hexane:ethyl acetate (1:1)] to give 12 mg of 1α-(ethylthio)-D-homo-17-oxaandrosta-4,6-dien-3-one as the less polar product.

¹H-NMR (CDCl₃, δ): 1.08 (3H, s), 1.23 (3H, t, J=7 Hz), 1.26 (3H, s), 2.3~3.6 (8H, m), 4.07 (1H, m), 5.72 (1H, s), 6.17 (2H, s)

Further, the more polar part was purified by TLC [developing solvent, chloroform:acetone (19:1)] to give 30 mg of 1α,7α-bis(ethylthio)-D-homo-17-oxaandrost-4-en-3-one as the less polar product.

¹H-NMR (CDCl₃, δ): 1.03 (3H, s), 1.23 (6H, t, J=7 Hz), 1.35 (3H, s), 2.2~3.7 (13H, m), 4.03 (1H, m), 5.79 (1H, s) MS (m/z): 408 (M⁺), 379, 346, 320, 284

Further, 19 mg of 7α-(ethylthio)-D-homo-17-oxaandrosta-1,4-dien-3-one was obtained as the more polar product.

¹H-NMR (CDCl₃, δ): 1.05 (3H, s), 1.22 (3H, t, J=7 Hz), 1.24 (3H, s), 2.3~3.6 (8H, m), 4.02 (1H, m), 6.10 (1H, br s), 6.26 (1H, dd, J=2, 10 Hz), 7.01 (1H, d, J=10 Hz) MS (m/z): 346 (M⁺), 284

Example 20

The same operations as in Example 19 were made using 2-aminoethanethiol in place of ethanethiol, and the resultant crude product was purified by TLC [developing solvent, chloroform:methanol (9:1)] to give 10 mg of 7α-[(2-aminoethyl)thio]-D-homo-17-oxaandrosta-1,4-dien-3-one.

¹H-NMR (CDCl₃, δ): 1.05 (3H, s), 1.24 (3H, s), 2.4~3.6 (12H, m), 4.00 (1H, m), 6.1 5 (1H, br s). 6.27 (1H, dd, J=2, 10 Hz), 7.02 (1H, d, J=10 Hz)

Example 21

The same operations as in Example 18 were made using methyl thioglycolate in place of thiophenol and dimethylformamide in place of dioxane, and the resultant crude product was purified by TLC [developing solvent, hexane:ethyl acetate (1:1)] and then TLC [developing solvent, chloroform:acetone (19:1)] to give 7α-(methoxycarbonylmethylthio)-D-homo-17-oxaandrosta-1,4-dien-3-one.

¹H-NMR (CDCl₃, δ): 1.05 (3H, s), 1.25 (3H, s), 2.6~2.8 (2H. m), 3.00 (1H, d, J=11 Hz), 3.16 (2H, d, J=1 Hz), 3.2~3.6 (3H, m), 3.71 (3H, s), 4.01 (1H, m), 6.08 (1H, br s), 6.27 (1H, d d, J=2, 10 Hz), 7.00 (1H, d, J=10 Hz) MS (m/z ): 390 (M⁺). 331, 284

Example 22

A mixture of 50 mg of D-homo-17-oxaandrosta-1,4,6-trien-3-one and 1 ml of thiobenzoic acid was heated to 60° C. in an atmosphere of nitrogen. Water was added to the reaction mixture, and the product was extracted with ethyl acetate. The extract was washed with aqueous 5% sodium bicarbonate solution and saturated saline, and dried over anhydrous magnesium sulfate. The solvent was distilled off, and the resultant crude product was purified by TLC [developing solvent, hexane:ethyl acetate (2:1)] to give 95 mg of 1α,7α-bis(benzoylthio)-D-homo-17-oxaandrost-4-en-3-one as the more polar product.

¹H-NMR (CDCl₃, δ): 1.04 (3H, s), 1.51 (3H, s), 2.5~3.5 (7H, m), 3.8~4.5 (3H, m), 5.77 (1H, s), 7.3~8.1 (10H, m) MS (m/z): 422 (M⁺-C₆H₅COSH), 284

Further, 4 mg of 1α-(benzoylthio)-D-homo-17-oxaandrosta-4,6-dien-3-one was obtained as the less polar product.

$^1$H-NMR (CDCl$_3$, δ): 1.06 (3H, s), 1.36 (3H, s), 2.5~3.6 (5H, m), 3.9~4.4 (2H, m), 5.77 (1H, s), 6.24 (2H, s), 7.3~8.0 (5H, m) MS (m/z ): 422 (M$^+$), 284

Example 23

A mixture of 50 mg of 7α-mercapto-D-homo-17-oxaandrosta-1,4-dien-3-one, 0.4 ml of pyridine and 0.2 ml of benzoyl chloride was stirred overnight at room temperature. Water and aqueous 5% hydrochloric acid solution were added to the reaction mixture, and the product was extracted with ethyl acetate. The extract was washed with water, and dried over anhydrous magnesium sulfate. The solvent was distilled off, and the resultant crude product was purified by TLC [developing solvent, hexane:ethyl acetate (1:1)] to give 57 mg of 7α-(benzoylthio)-D-homo-17-oxaandrosta-1,4-dien-3-one.

$^1$H-NMR (CDCl$_3$, δ): 1.08 (3H, s), 1.30 (3H, s), 2.55 (1H, dd, J=3, 14 Hz), 2.8~3.5 (4H, m), 3.94 (1lt. m), 4.34 (1H, m), 6.04 (1H, br s), 6.30 (1H, dd, J=2, 10 Hz), 7.04 (1H, d, J=10 Hz), 7.3~8.2 (5H, m) MS (m/z): 422 (M$^+$), 284

Example 24

A mixture of 10 mg of 7α-(methylthio)-D-homo-17-oxaandrosta-1,4-dien-3-one, 5 mg of m-chloroperbenzoic acid and 0.6 ml of benzene was stirred at 10° C. for 10 minutes. Water was added to the reaction mixture, and the product was extracted with ethyl acetate. The extract was washed with aqueous 5% sodium bicarbonate solution and saturated saline, and dried over anhydrous sodium sulfate. The solvent was distilled off, and the resultant crude product was purified by TLC [developing solvent, chloroform:methanol (15:1)] to give 3 mg of 7α-(methyl sulfinyl)-D-homo-17-oxaandrosta-1,4-dien-3-one as the more polar product.

$^1$H-NMR (CDCl$_3$, δ): 1.05 (3H, s), 1.30 (3H, s), 2.66 (3H, s), 2.4~3.7 (6H, m), 3.97 (1H, m), 5.94 (1H, br s), 6.29 (1H, dd, J=2, 10 Hz), 7.10 (1H, d, J=10 Hz) MS (m/z): 348 (M$^+$), 285

Further, 1 mg of 7α-(methylsulfonyl)-D-homo-17-oxaandrosta-1,4-dien-3-one was obtained as the less polar product.

$^1$H-NMR (CDCl$_3$, δ): 1.05 (3H, s), 1.26 (3H, s), 2.89 (3H, s), 2.7~3.8 (5H, m), 4.03 (1H, m), 6.17 (1H, br s), 6.29 (1H, dd, J=2, 10 Hz) 7.07 (1H, d, J=10 Hz) MS (m/z): 364 (M$^+$), 284

Example 25

A mixture of 10 mg of 7α-(methylthio)-D-homo-17-oxaandrosta-1,4-dien-3-one and 0.2 ml of thioacetic acid was stirred at room temperature for one hour in an atmosphere of nitrogen. Water was added to the reaction mixture, and the product was extracted with ethyl acetate. The extract was washed with aqueous 5% sodium bicarbonate solution and saturated saline, and dried over anhydrous magnesium sulfate. The solvent was distilled off, and the resultant crude product was purified by TLC [developing solvent, chloroform:acetone (19:1)] to give 12 mg of 1α-(acetylthio)-7α-(methylthio)-D-homo-17-oxaandrost-4-en-3-one.

$^1$H-NMR (CDCl$_3$, δ): 1.01 (3H, s), 1.40 (3H, s), 2.05 (3H, s), 2.34 (3H, s), 2.4~3.6 (8H, m), 3.9~4.2 (2H, m), 5.80 (1H, br s) MS (m/z): 408 (M$^+$), 284

Example 26

A mixture of 15 mg of 7α-mercapto-D-homo-17-oxaandrost-4-ene-3,17a-dione, 0.75 ml of pyridine and 0.05 ml of propionic anhydride was stirred overnight under N$_2$ at room temperature. Water and aqueous 5% hydrochloric acid solution were added to the reaction mixture, and the product was extracted with ethyl acetate. The extract was washed with aqueous 5% sodium bicarbonate solution and saturated saline, and dried over anhydrous sodium sulfate. The solvent was distilled off, and the resultant crude product was purified by TLC [developing solvent, hexane:ethyl acetate (1:1)] to give 3 mg of 7α-(propionylthio)-D-homo-17-oxaandrost-4-ene-3,17a-dione.

$^1$H-NMR (CDCl$_3$, δ): 1.17 (3H. t, J=7.5Hz), 1.22 (3H, s), 1.26 (3H, s), 2.58 (2H, q, J=7.5Hz), 2.9 (1H, m), 4.0~4.6 (3H, m), 5.72 (1H, d, J=2 Hz) MS (m/z): 390 (M$^+$), 357, 334

Example 27

The same operations as in Example 26 were made using dimethylcarbamoyl chloride in place of propionic anhydride to give 17 mg of 7α-(N,N-dimethylcarbamoylthio)-D-homo-17-oxaandrost-4-ene-3,17a-dione.

$^1$H-NMR (CDCl$_3$, δ): 1.22 (3H, s), 1.27 (3H, s), 3.00 (6H, s), 4.0~4.6 (3H, m), 5.76 (1H, d, J=1.5 Hz) MS (m/z):405 (M$^+$), 390, 372, 333

Example 28

The same operations as in Example 26 were made using ethyl chlorocarbonate in place of propionic anhydride to give 9 mg of 7α-(ethoxycarbonylthio)-D-homo-17-oxaandrost-4-ene-3,17a-dione.

$^1$H-NMR (CDCl$_3$, δ): 1.22 (3H, s), 1.27 (3H, s), 1.31 (3H, t, J=7 Hz), 2.57 (1H, dd, J=3, 10 Hz), 2.88 (1H, ddd, J=1.8, 4, 15Hz), 3.8~4.0 (1H, m), 4.26 (2H, q, J=7 Hz), 4.0~4.6 (2H, m), 5.78 (1H, m) MS (m/z):406 (M$^+$), 391, 362, 347

Example 29

A mixture of 15 mg of D-homo-17-oxaandrosta-4,6-diene-3,17a-dione,1 μl of 28% sodium methylate methanol solution, 30 μl of allylmercaptan and 0.23 ml of dioxane was stirred under N$_2$ at room temperature for 3 days. Water and aqueous 5% hydrochloric acid solution were added to the reaction mixture, and the product was extracted with ethyl acetate. The extract was washed with aqueous 5% sodium bicarbonate solution and saturated saline, and dried over anhydrous sodium sulfate. The solvent was distilled off, and the resultant crude product was purified by TLC [developing solvent, hexane ethyl acetate (1:1)] to give 10 mg of 7α-(allylthio)-D-homo-17-oxaandrost-4-ene-3,17a-dione.

$^1$H-NMR (CDCl$_3$, δ): 1.20 (3H, s), 1.25 (3H, s), 3.0~3.2 (3H, m), 4.1~4.7 (2H, m), 5.08 (1H, dd, J=1.3, 15 Hz), 5.11 (1H, dd, J=1.8, 11 Hz), 5.4~6.1 (1H, m), 5.78 (1H, br s) MS (m/z):374 (M$^+$), 359, 341, 333

Example 30

The same operations as in Example 29 were made using ethanethiol in place of allylmercaptan, and the resultant crude product was purified by TLC [developing solvent, hexane:ethyl acetate (2:1)] to give 6 mg of 7α-(ethylthio)-D-homo-17-oxaandrost-4-ene-3,17a-dione.

$^1$H-NMR (CDCl$_3$, δ) :1.21 (3H, s), 1.24 (3H, t, J=7 Hz), 1.26 (3H, s), 2.3~2.7 (4H, m), 3.1~3.2 (1 H, m), 4.1~4.6 (2H, m), 5.7 8 (1H, br s) MS (m/z):362 (M$^+$), 347, 333

Example 31

The same operations as in Example 29 were made using 2-mercaptoethanol in place of allylmercaptan, and the resultant crude product was purified by TLC [developing solvent, chloroform:methanol (9:I)] to give 4 mg of 7α-[(2-hydroxyethyl)thio]-D-homo-17-oxaandrost-4-ene-3,17a-dione.

$^1$H-NMR (CDCl$_3$, δ): 1.21 (3H, s), 1.26 (3H, s), 2.70 (2H, t, J=6 Hz), 3.1~3.3 (1H, m), 3.74 (2H, t, J=6 Hz), 4.1~4.7 (2H, m), 5.79 (1H, br s) MS (m/z): 378 (M$^+$), 363, 360, 348

Example 32

A mixture of 15 mg of 7α-mercapto-D-homo-17-oxaandrosta-1,4-diene-3,17a-dione, 0.75 ml of pyridine and 0.05 ml of benzoyl chloride was stirred overnight under N$_2$ at room temperature. Water and aqueous 5% hydrochloric acid solution were added to the reaction mixture, and the product was extracted with ethyl acetate. The extract was washed with aqueous 5% sodium bicarbonate solution and saturated saline, and dried over anhydrous sodium sulfate. The solvent was distilled off, and the resultant crude product was purified by TLC [developing solvent, chloroform:acetone (19:1)] and then TLC [developing solvent, hexane:ethyl acetate (1:1)] to give 12 mg of 7α-(benzoylthio)-D-homo-17-oxaandrosta-1,4-diene-3,17a-dione.

$^1$H-NMR (CDCl$_3$, δ): 1.30 (3H, s), 1.31 (3H, s), 2.55 (1H, dd, J=2.9, 14 Hz), 3.05 (1H, ddd, J=1.5, 4, 14 Hz), 2.9~3.6 (3H, m), 6.07 (1H, br s), 6.30 (1H, dd, J=2, 10 Hz), 7.06 (1H, d, J=10 Hz), 7.3~7.7 (3H, m), 7.8~8.0 (2H, m) MS (m/z): 436 (M$^+$), 421, 403

Example 33

The same operations as in Example 32 were made using propionic anhydride in place of benzoyl chloride to give 11 mg of 7α-(propionylthio)-D-homo-17-oxaandrosta-1,4-diene-3,17a-dione.

$^1$H-NMR (CDCl$_3$, δ): 1.17 (3H, t, J=8 Hz), 1.26 (3H, s), 1.29 (3H, s), 2.58 (2H, q, J=8 Hz), 2.97 (1H, ddd, J=1.5, 4, 14 Hz), 4.0~4.6 (3H, m), 6.05 (1H, t, J=1.5 Hz, 6.27 (1H, dd, J=2, 10 Hz), 7.02 (1H, d, J=10 Hz) MS (m/z):389 (MH$^+$), 360, 332

Example 34

The same operations as in Example 32 were made using dimethylcarbamoyl chloride in place of benzoyl chloride to give 17 mg of 7α-(N,N-dimethylcarbamoylthio)-D-homo-17-oxaandrosta-1,4-diene-3,17a-dione.

$^1$H-NMR (CDCl$_3$, δ) :1.26 (3H, s), 1.30 (3H, s), 2.99 (6H, s), 4.0~4.6 (3H, m), 6.09 (1H, t, J=1.5 Hz), 6.27 (1H, dd, J=2, 10 z), 7.04 (1H, d, J=10 Hz) MS (m/z):403 (M$^+$), 388, 370, 332

Example 35

The same operations as in Example 32 were made using ethyl chlorocarbonate in place of benzoyl chloride to give 14 mg of 7α-(ethoxycarbonylthio)-D-homo-17-oxaandrosta-1,4-diene-3,17a-dione.

$^1$H-NMR (CDCl$_3$, δ): 1.2 6 (3H, s), 1.30 (3H, s), 1.31 (3H, t, J=7 Hz), 2.61 (1H, dd, J=3, 14 Hz), 2.97 (1H, ddd, J=1.3, 4, 14), 3.8~4.6 (3H, m), 4.28 (2H, q, J=7 Hz), 6.11 (1H, t, J=1.5 Hz), 6.27 (1H, dd, J=2, 10 Hz), 7.02 (1H, d, J=10 Hz) MS (m/z): 405 (MH$^+$), 375, 360

Example 36

The same operations as in Example 29 were made using D-homo-17-oxaandrosta-1,4,6-triene-3,17a-dione in place of D-homo-17-oxaandrosta-4,6-di ene-3,17a-dione, and the resultant crude product was purified by TLC [developing solvent, hexane:ethyl acetate (1:1)] to give 1 mg of 7α-(allylthio)-D-homo-17-oxaandrosta-1,4-diene-3,17a-dione as the more polar product.

$^1$H-NMR (CDCl$_3$, δ): 1.24 (3H, s), 1.27 (3H, s), 2.53 (1H, dd, J=3, 14 Hz), 2.80 (1H, ddd, J=1.3, 4, 14 Hz), 3.0~3.3 (3H, m), 4.1~4.6 (2H, m), 4.9~5.2 (2H, m), 5.5~6.1 (1H, m), 6.12 (1H, t, J=1.3 Hz), 6.27 (1H, dd, J=2, 10 Hz), 7.02 (1H, d, J=10 Hz) MS (m/z): 372 (M$^+$), 358, 339, 331

Further, the less polar part was purified by TLC [developing solvent, benzene:ethyl acetate (4:1)] to give 14 mg of 1α,7α-bis(allylthio)-D-homo-17-oxaandrost-4-ene-3,17a-dione as the more polar product.

$^1$H-NMR (CDCl$_3$, δ): 1.25 (3H, s), 1.34 (3H, s), 2.5~3.2 (10H, m), 4.1~4.7 (2H, m), 4.9~5.2 (4H, m), 5.4~6.0 (2H, m), 5, 81 (1H, br s)

Further, 4 mg of 1α-(allylthio)-D-homo-17-oxaandrosta-4,6-diene-3,17a-dione was obtained as the less polar product.

$^1$H-NMR (CDCl$_3$, δ): 1.25 (3H, s), 1.31 (3H, s), 2.5~3.0 (2H, m), 3.0~3.2 (3H, m), 4.1~4.7 (2H, m), 4.9~5.3 (2H, m), 5.5~6.1 (1H, m), 5.74 (1H, s), 6.18 (2H, br s)

Example 37

To a mixture of 2ling of 7α-mercapto-D-homo-17-oxaandrost a-1,4-diene-3,17a-dione, 19 μl of 28% sodium methylate methanol solution and 0.45 ml of methanol was added 4 μl of ethyl bromide, and the mixture was stirred at room temperature for 5 minutes in an atmosphere of nitrogen. Aqueous 3.6% hydrochloric acid solution was added to the reaction mixture, and the product was extracted with ethyl acetate. The extract was washed with aqueous 5% sodium bicarbonate solution and saturated saline, and dried over anhydrous magnesium sulfate. The solvent was distilled off, and the resultant crude product was purified by TLC [developing solvent, chloroform:acetone (19:1)] to give 8 mg of 7α-(ethylthio)-D-homo-17-oxaandrosta-1,4-diene-3,17a-dione.

$^1$H-NMR (CDCl$_3$, δ): 1.24 (3H, s), 1.28 (3H, s), 2.3~3.0 (4H, m), 3.1~3.3 (1H, m), 4.1~4.7 (2H, m), 6.11 (1H, t, J=1.5 Hz), 6.26 (1H, dd, J=2, 10 Hz), 7.03 (1H, d, J=10 Hz) MS (m/z): 360 (M$^+$), 345, 332

Example 38

To a mixture of 21 mg of 7α-mercapto-D-homo-17-oxaandrosta-1,4-diene-3,17a-dione, 14 μl of 28% sodium methylate methanol solution and 1 ml of dimethylformamide was added 30 μl of ethylenebromohydrine, and the mixture was stirred at room temperature for 5 minutes in an atmosphere of nitrogen. Aqueous 3.6% hydrochloric acid solution was added to the reaction mixture, and the product was extracted with ethyl acetate. The extract was washed with aqueous 5% sodium bicarbonate solution and saturated saline, and dried over anhydrous magnesium sulfate. The solvent was distilled off, and the resultant crude product was purified by TLC [developing solvent, chloroform:acetone (4:1)] to give 12 mg of 7α-[(2-hydroxyethyl)thio]-D-homo-17-oxaandrosta-1,4-diene-3,17a-dione.

$^1$H-NMR (CDCl$_3$, δ): 1.25 (3H, s), 1.28 (3H, s), 2.70 (2H, t, J=6 Hz), 2.5~3.0 (2H, m), 3.2~3.4 (2H, m), 3.6~3.9 (2H, br m), 4.1~4.7 (2H, m), 6.12 (1H, t, J=1.3 Hz), 6.27 (1H, dd, J=2, 10 Hz), 7.04 (1H, d, J=10 Hz) MS (m/z): 376 (M$^+$), 361, 346, 331

Example 39

The same operations as in Example 38 were made using ethyl bromoacetate in place of ethylenebromohydrine, and the resultant crude product was purified by TLC [developing solvent, chloroform:acetone (19:1)] to give 2 mg of 7α-(ethoxycarbonylmethylthio)-D-homo-17-oxaandrosta-1,4-diene-3,17a-dione.

$^1$H-NMR (CDCl$_3$, δ): 1.25 (3H, s), 1.28 (3H, s), 2.61 (1H, dd, J=3, 14 Hz), 2.86 (1H, ddd, J=1.5, 3, 14 Hz), 3.18, 3.21 (2H, AB q J=15 Hz), 3.4~3.6 (1H, m), 3.73 (3H, s), 4.1~4.7 (2H, m), 6.10 (1H, br m), 6.27 (1 H, dd, J=1.8, 10 Hz), 7.02 (1H, d, J=10 Hz) MS (m/z ): 404 (M$^+$), 389, 372, 345

Example 40

The same operation s as in Example 38 were made using methyl iodide in pl ace of ethylenebromohydrine, and the resultant crude product was purified by TLC [developing solvent, hexane:ethyl acetate (1:1)] to give 15 mg of 7α-(methylthio)-D-homo-17-oxaandrost a-1,4-diene-3,17a-dione.

$^1$H-NMR (CDCl$_3$, δ): 1.25 (3H, s), 1.28 (3H, s), 2.04 (3H, s), 2.5~2.9 (2H, m), 3.04~3.2 (1H, m), 4.0~4.6 (2H, m), 6.12 (1H, br s), 6.27 (1H, dd, J=1.8, 10 Hz), 7.03 (1H, d, J=10 Hz) MS (m/z): 346 (M$^+$), 331, 300, 298

Example 41

A mixture of 13 mg of 7α-(methylthio)-D-homo-17-oxaandrosta-1,4-diene-3,17a-dione, 6.5 mg of m-chloroperbenzoic acid and 0.8 ml of anhydrous benzene was stirred at room temperature for 20 minutes. The solvent was distilled off from the reaction mixture, and the resultant crude product was purified by TLC [developing solvent, chloroform:methanol (9:1)] to give 7 mg of 7α-(methylsulfinyl)-D-homo-17-oxaandrosta-1,4-diene-3,17a-dione.

$^1$H-NMR (CDCl$_3$, δ) :1.28 (3H, s), 1.30 (3H, s), 2.69 (3H, s), 3.2~3.4 (1H, m), 4.24~4.5 (2H, m), 5.9~6.0 (1H, m), 6.29 (1H, dd, J=1.8, 10 Hz), 7.11 (1H, d, J=10 Hz) MS (m/z): 362 (M$^+$), 346, 344

Example 42

A mixture of 14 μl of 28% sodium methylate methanol solution and 1 ml of dimethylformamide was cool ed to –20° C., and under N$_2$, a largely excess amount of methanethiol was added and the mixture was stirred for 5 minutes. To this reaction mixture was added 15 mg of D-homo-17-oxaandrosta-1,4,6-triene-3,17a-dione, and the mixture was stirred at room temperature for 3 days. Water and aqueous 5% hydrochloric acid solution were added to the reaction mixture, and the product was extracted with ethyl acetate. The extract was washed with aqueous 5% sodium bicarbonate solution and saturated saline, and dried over anhydrous sodium sulfate. The solvent was distilled off, and the resultant crude product was purified by TLC [developing solvent, hexane:ethyl acetate (1:1)] to give 20 mg of 1α,7α-bis(methylthio)-D-homo-17-oxaandrost-4-ene-3,17a-dione.

$^1$H-NMR (CDCl$_3$, δ): 1.26 (3H, s), 1.36 (3H, s), 2.07 (3H, s), 2.09 (3H, s), 2.4~3.2 (6H, m), 4.1~4.6 (2H, m), 5.82 (1H, br s) MS (m/z): 394 (M$^+$), 379, 347, 320

Example 43

A mixture of 2g of D-homo-17-oxaandrosta-1,4,6-triene-3,17a-dione and 8 ml of thioacetic acid was refluxed for 4 hours. The reaction mixture was left to cool and poured into ice water wherein 4.8 g of sodium hydroxide had been dissolved, and the product was extracted with ethyl acetate. The extract was washed with aqueous 5% sodium bicarbonate solution and saturated saline, and dried over anhydrous magnesium sulfate. The solvent was distilled off, and the resultant crude product was crystallized from diethy etherethyl acetate to give 2.45 g of 1α,7α-bis(acetylthio)-D-homo-17-oxaandrost-4-ene-3,17a-dione.

$^1$H-NMR (CDCl$_3$, δ): 1.25 (3H, s), 1.40 (3H, s), 2.36 (3H, s), 2.39 (3H, s), 4.0~4.7 (4H, m), 5.74 (1H, br s) MS (m/z): 451 (MH$^+$), 407, 390, 375

The resultant mother liquor was purified by TLC [developing solvent, hexane:ethyl acetate (1:1)] to give 106 mg of 1α-(acetylthio)-D-homo-17-oxaandrosta-4,6-diene-3,17a-dione.

$^1$H-NMR (CDCl$_3$, δ): 1.30 (6H, s), 2.32 (3H, s), 2.67 (1H, ddd, J=1,2.6, 18 Hz), 3.1 2 (1H, dd, J=4, 18 Hz), 4.0~4.2 (1H, m), 4.2~4.7 (2H, m), 5.74 (1H, s), 6.20 (2H, s) MS (m/z): 374 (M$^+$), 346, 341, 332

Example 44

A mixture of 1 g of 1α,7α-bis(acetylthio)-D-homo-17-oxaandrost-4-ene-3,17a-dione, 1.8 ml of 28% sodium methyl ate methanol solution and 10 ml of methanol was stirred at room temperature for 30 minutes in an atmosphere of nitrogen. The reaction mixture was poured into aqueous 3.6% hydrochloric acid solution, and the product was extracted with ethyl acetate. The extract was washed with aqueous 5% sodium bicarbonate solution and saturated saline, and dried over anhydrous magnesium sulfate. The solvent was distilled off, and the resultant crude product was purified by silica gel column chromatography [eluting solvent, chloroform] to give 694 mg of 7α-mercapto-D-homo-17-oxaandrosta-1,4-diene-3,17a-dione.

Melting point: 207°–211° C. (dichloromethaneethyl acetate)

$^1$H-NMR (CDCl$_3$, δ): 1.24 (3H, s), 1.30 (3H, s), 2.54 (1H, dd, J=2, 14 Hz), 3.04 (1H, m), 3.43 (1H, m), 4.0~4.6 (2H, m), 6.15 (1H, br t, J=2 Hz), 6.30 (1, dd, J=2, 10 Hz), 7.03 (1H, d, J=10 Hz) MS (m/z): 332 (M$^+$), 317, 298, 283

Elementary analysis:

Calculated for C$_{19}$ H$_{24}$O$_3$S: C, 68.64: H, 7.28 Found: C, 68.64: H,7.28

Preparation Example 1

A mixture of 2.0 g of D-homo-17-oxaandrosta-4,6-diene-3,17a-dione, 4.6 g of lithium tri-tert-butoxyaluminohydride and 100 ml of tetrahydrofuran was stirred at 0° C. for 20 minutes. Water and 5% hydrochloric acid were added to the reaction mixture, and the product was extracted with ethyl acetate. The extract was washed with aqueous 5% sodium bicarbonate solution and saturated saline, and dried over anhydrous magnesium sulfate. The solvent was distilled off to give 1.8 g of 17aξ-hydroxy-D-homo-17-oxaandrost a-4,6-dien-3-one.

Preparation Example 2

A mixture of 1.8 g of 17aξ-hydroxy-D-homo-17-oxaandrost a-4,6-dien-3-one, 12 ml of pyridine and 6 ml of acetic anhydride was stirred at room temperature for 15 hours.

Water was added to the reaction mixture, and the product was extracted with ethyl acetate. The extract was washed with 3% hydrochloric acid, aqueous 5% sodium bicarbonate solution and saturated saline, and dried over anhydrous magnesium sulfate. The solvent was distilled off, and the resultant crude product was purified by TLC [developing solvent, chloroform:acetone (39:1)] to give 1.73 g of 17aξ-acetoxy-D-homo-17-oxaandrosta-4,6-dien-3-one.

Preparation Example 3

The same operations as in Example 6 were made using 800 mg of 17aξ-acetoxy-D-homo-17-oxaandrosta-4,6-dien-3-one in place of D-homo-17-oxaandrosta-4,6-dien-3-one, and the resultant crude product was purified by TLC [developing solvent, benzene:ethyl acetate (1:1)] to give 106 mg of 7α-benzyl-17aξ-hydroxy-D-homo-17-oxaandrost-4-en-3-one.

Preparation Example 4

Water was gradually azeotropically removed from a mixture of 2.0 g of D-homo-17-oxaandrost-4-en-3-one, 100 ml of ethylene glycol, 500 mg of p-toluenesulfonic acid and 400 ml of benzene using a Dean-Stark apparatus. Aqueous 5% sodium bicarbonate solution was added to the reaction mixture, and the product was extracted with ethyl acetate. The extract was washed with saturated saline, and dried over anhydrous magnesium sulfate. The solvent was distilled off to give 2.4 g of 3,3:17a,17a-bis(ethylenedioxy)-D-homo-17-oxaandrost-5-ene.

$^1$H-NMR (CDCl$_3$, δ): 1.02 (3H, s), 1.11 (3H, s), 3.6~4.3 (10H, m), 5.33 (1H, m) MS (m/z): 390 (M$^+$), 345, 302

Preparation Example 5

A mixture of 13.3 g of chromium oxide, 22 ml of pyridine and 210 ml of methyl ene chloride was stirred at room temperature for 20 minutes in an atmosphere of nitrogen. To the mixture was added a mixture of 2.4 g of 3,3: 17a,17a-bis(ethylenedioxy)-D-homo-17-oxaandrost-5 -ene and 88 ml of methylene chloride, and the mixture was stirred for 5 days. Diethyl ether was added to the reaction mixture, the insoluble matter was filtered off, and the filtrate was washed with 3% hydrochloric acid, aqueous 5% sodium bicarbonate solution and saturated saline, and dried over anhydrous sodium sulfate. The solvent was distilled off, and the residue was recrystallized from acetone-diethyl ether to give 870 mg of 3,3:17a, 17a-bis(ethylenedioxy)-D-homo-17-oxaandrost-5 -en-7-one.

$^1$H-NMR (CDCl$_3$, δ): 1.11 (3H, s), 1.2 2 (3H, s), 3.5~4.4 (10H, m), 5.6 3 (1H, br s)

Preparation Example 6

125 ml of 2.0M benzyl magnesium chloride tetrahydrofuran solution was added dropwise over period of 20 minutes to a mixture of 200 mg of 3,3:17a,17a-bis(ethylenedioxy)-D-homo-17-oxaandrost-5-en-7-one and 17.6 ml of tetrahydrofuran at room temperature in an atmosphere of nitrogen. The reaction mixture was poured into aqueous saturated ammonium chloride solution, and the product was extracted with diethyl ether. The extract was washed with saturated saline, and dried over anhydrous sodium sulfate. The solvent was distilled off to give 240 mg of 7ξ-benzyl-3,3:17a,17a-bis(ethylenedioxy)-D-homo-17-oxaandrost-5-en-7ξ-ol.

Preparation Example 7

The same operations as in Preparation Example 1 were made using 30 mg of 7-benzyl-D-homo-17-oxaandrosta-4,6-diene-3,17a-dione in place of D-homo-17-oxaandrosta-4,6-diene-3,17a-dione to give 30 mg of 7-benzyl-17aξ-hydroxy-D-homo-17-oxaandrosta-4,6-dien-3-one.

A preparation example of a pharmaceutical containing a compound of this invention is shown below.

| Preparation example A: Tablet | mg/tablet |
|---|---|
| Active ingredient | 100 |
| Starch | 20 |
| Lactose | 105.5 |
| Carboxymethylcellulose calcium | 20 |
| Talc | 3 |
| Magnesium stearate | 1.5 |
| | 250 mg |

The active ingredient is pulverized into a particle size of 70 microns or less, and to this were added starch, lactose and carboxymethylcellulose calcium, and the mixture is sufficiently mixed. 10% of starch paste is added to the mixed fine particles, the mixture is mixed, and granules are prepared. After being dried, the granules are gradede into a particle size of around 1,000 microns, talc and magnesium stearate are mixed therewith, and the mixture is tableted.

Industrial Applicability

The compounds of the above-mentioned formula (I) of this invention have an aromatase-inhibiting action, and are useful for prophylaxis and treatment of diseases caused by estrogens, for example breast cancer, uterine cancer, prostatic hypertrophy.

We claim:

1. A steroid compound represented by the formula

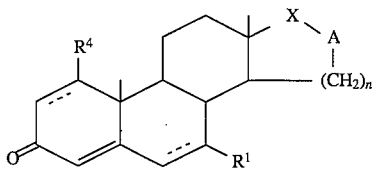

wherein $R^1$ denotes —S—$R^2$, —S(O)$_m$—$R^3$ or a benzyl, 4-methoxybenzyl or phenethyl group, $R^2$ denotes a hydrogen atom; a lower alkyl group optionally substituted with a hydroxyl, amino or lower alkoxycarbonyl group; a lower alkenyl group; a benzyl, 4-methoxybenzyl or phenethyl group; a phenyl or naphthyl group optionally substituted with halogen atom(s), or amino, di-(lower alkyl)amino, lower alkoxy or lower alkyl group(s); —COR$^6$; or a lower alkoxycarbonyl group, $R^3$ denotes a lower alkyl group, m denotes 1 or 2, $R^4$ denotes a hydrogen atom or —S—$R^5$, $R^5$ denotes a lower alkyl group optionally substituted with a hydroxyl, amino or lower alkoxycarbonyl group; a lower alkenyl group; a benzyl, 4-methoxybenzyl or phenethyl group; a phenyl or naphthyl group optionally substituted with halogen atom(s), or amino, di-(lower alkyl)amino, lower alkoxy or lower alkyl group(s); or —COR$^6$, R$^6$ denotes a hydrogen atom; a lower alkyl group optionally substituted with a halogen atom, an amino group, a carboxyl group, a lower alkoxycarbonyl group, a lower alkanoyloxy group, a carbamoyl group or a phenyl group; a lower alkenyl group optionally substituted with a phenyl group; a lower cycloalkyl group; a phenyl group optionally substituted with lower alkyl group(s), lower alkoxy group(s) or halogen atom(s); an amino group optionally substituted with one or two lower alkyl groups, X denotes C=O or CH$_2$, A denotes O, n denotes 2, and the broken lines between the 1- and 2-positions and between the 6- and 7-positions of the steroid skeleton mean that a double bond can optionally exist there, provided that (a) when R$^1$ denotes —S—R$^2$ or —S(O)$_m$—R$^3$, the bond between the 6- and 7-positions denotes a single bond, and (b) when R$^4$ denotes —S—R$^5$, the bond between the 1- and 2-positions denotes a single bond.

2. The steroid compound according to claim 1 wherein R$^1$ denotes —S—R$^2$ or —S(O)$_m$—R$^3$.

3. The steroid compound according to claim 1 wherein the substituent R$^1$ binds to the α-position.

4. An aromatase inhibitor which comprises a compound according to claim 1 and pharmaceutically acceptable additive(s).

5. A pharmaceutical composition which comprises a compound according to claim 1 and pharmaceutically acceptable additive(s).

6. A method for prophylaxis or treatment of a disease in a human being or other mammal caused by an estrogen, which comprises administering to the human being or other mammal an effective amount of a compound according to claim 1.

* * * * *